United States Patent
Sijbesma et al.

(12)

(10) Patent No.: US 6,320,018 B1
(45) Date of Patent: Nov. 20, 2001

(54) SUPRAMOLECULAR POLYMER

(75) Inventors: Rintje P. Sijbesma, Den Bosch; Felix H. Beijer; Lucas Brunsveld, both of Eindhoven; Egbert W. Meijer, Waalre, all of (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 09/285,781

(22) Filed: Apr. 5, 1999

Related U.S. Application Data

(63) Continuation of application No. PCT/NL97/00535, filed on Sep. 25, 1997.

(30) Foreign Application Priority Data

Oct. 4, 1996 (NL) ..................................... 1004192

(51) Int. Cl.[7] .......................... C08G 77/26; C08G 77/54; C08G 83/00
(52) U.S. Cl. .......................... 528/310; 528/172; 528/183; 528/229; 528/315
(58) Field of Search ..................................... 528/310, 172, 528/183, 229, 315

(56) References Cited

FOREIGN PATENT DOCUMENTS

433188 A * 6/1991 (EP) .
2657082 * 7/1991 (FR) .

OTHER PUBLICATIONS

Derwent 91–179975125.*
Urbanski, et al. "Potential Antimalarial Compounds[1]. IX[2]. Pyrimidine Derivatives of Urea and Guanidine", Journal of Medicinal Chemistry, vol. 10, 1967, pp. 521–525.
Chemical Abstract, vol. 85, Abst. No. 15348y (Jul. 1976).

* cited by examiner

*Primary Examiner*—P. Hampton-Hightower
(74) *Attorney, Agent, or Firm*—Pillsbury Winthrop LLP

(57) ABSTRACT

A polymer comprising monomeric units linked via 4 H-bridges and bound within said polymer via a different bond. The bond via the H-bridges is much stronger than with known supramolecular polymers.

14 Claims, No Drawings

SUPRAMOLECULAR POLYMER

This is a Continuation of International Appln. No. PCT/NL97/00535 filed Sep. 25, 1997 which designated the U.S.

FIELD OF THE INVENTION

BACKGROUND OF THE INVENTION

The invention relates to a supramolecular polymer containing monomeric units that form H-bridges with one another.

Such polymers are described in Lehn J.-M. Angew. Chem. 1988, 100.91, which describes polymers based on monomeric units that form 3 H-bridges with one another.

A drawback of the polymers described in the aforementioned publication is that even these 3-fold H-bridges do not associate sufficiently for many possible applications of supramolecular polymers. It has been found that no association constants higher than $10^5$ $M^{-1}$ can be realized for 3-fold H-bridges with neutral molecules. These supramolecular polymers have thus shown no properties characteristic of polymers with only covalent bonds between the monomers. In addition, the synthesis of the building blocks that associate the most strongly is particularly difficult and cannot be carried out on a large scale.

SUMMARY OF THE INVENTION

The invention now provides polymers containing H-bridge-forming monomeric units in which the bond via the H-bridges is much stronger than with the known supramolecular polymers.

This is achieved according to the invention by using H-bridge-forming monomers which, in pairs, form at least 4 H-bridges with one another.

The term "supramolecular polymer" is understood to mean an organic compound that obtains its polymeric properties, for example with respect to mechanical strength, etc., essentially through a combination of covalent bonds and secondary specific interactions, the latter preferably having a high bond strength and contributing substantially to the polymeric behaviour.

There has for many years been an interest in supramolecular polymers in which the monomers are at least in part bound to one another via H-bridges.

Advantages of such polymers are that, in principle, materials with polymeric properties can be obtained in which the bond via the H-bridges can be used in a reversible manner, and that the polymer can be composed from simple low-molecular-weight units. As the H-bridges are much weaker at higher temperatures, implying a more rapid exchange between monomers than at low temperatures, an important advantage is obtained in processing: at higher temperatures only monomeric units (that can be easily handled) are essentially present which, when the temperature is lowered, form a rigid, dimensionally stable polymer. The "polymerisation step" takes place under mild conditions in comparison with the polymerisation of polymers that are only covalently bound, and is greatly simplified because no catalysts or other additives have to be added.

DETAILED DESCRIPTION OF THE INVENTION

In a supramolecular polymer, H-bridge-forming monomeric units are, with the exception of the polymeric ends, bound via at least 2 bonds ("on at least 2 sides"). An H-bridge-forming monomeric unit is in the context of this invention understood to be a unit that is on at least one side linked via at least 4 H-bridges to another H-bridge-forming monomeric unit in the supramolecular polymer, and is moreover on at least one side bound in the supramolecular polymer via a different, for example covalent, bond. In the case of a linear supramolecular polymer consisting exclusively of H-bridge-forming monomeric units the H-bridge-forming monomeric units are for example bound on 2 sides to the adjacent H-bridge-forming monomeric unit, with there being a covalent bond on one side and on the other side a bond via at least 4 H-bridges.

The H-bridge-forming monomeric units that can be used in the process according to the invention may be self-complementary, which means that at least 2 identical monomeric units form at least 4 H-bridges with one another; it is however also possible for the supramolecular polymer to contain 2 (or more) different types of H-bridge-forming monomeric units, with 2 different monomeric units always forming at least 4 H-bridges with one another. A combination is of course also possible. Preferably, the H-bridges are oriented parallel to one another. Particularly suitable H-bridge-forming monomeric units are those units that contain a structural element having the general form (1) or (2)

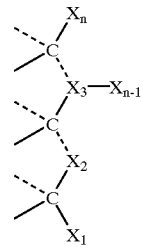

(1)

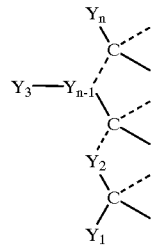

(2)

in which the C-Xi and C-Yi linkages each represent a single or double bond, n is 4 or more and $X_1 \ldots X_n$ represent donors or acceptors that form H-bridges with the H-bridge-forming monomeric unit containing a corresponding structural element (2) linked to them, with $X_i$ representing a donor and $Y_i$ an acceptor and vice versa.

The H-bridge-forming monomeric units preferably have an essentially flat, rigid structure; in particular, the monomeric unit preferably contains one or more flat 6-rings and/or one or more H-bridges. In a linear supramolecular polymer the bonds preferably associate via the H-bridges only in the direction of the supramolecular polymer chain.

The invention is in particular aimed at H-bridge-forming monomeric units having 4 donors or acceptors, so that they can in pairs form 4 H-bridges with one another. Preferably the H-bridge-forming monomeric units have 2 successive donors, followed by 2 acceptors, for example monomeric units according to formula 1 with n=4, in which $X_1$ and $X_2$ both represent a donor and an acceptor, respectively, and $X_3$ and $X_4$ both an acceptor and a donor, respectively.

A particularly suitable H-bridge-forming monomeric unit that can be used in the polymers according to the invention is the compound (3.a) or the tautomeric form (3.b) thereof:

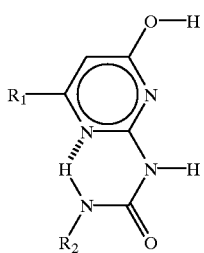

3.a

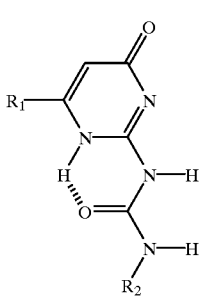

3.b

The H-bridge-forming monomeric units according to formulas 3.a and 3.b, respectively, may be bound in the supramolecular polymer in various ways. These H-bridge-forming monomeric units may for example be bound in the supramolecular polymer via a linking unit $R_2$, with $R_1$ representing a random side chain, or vice versa, while it is also possible for the supramolecular polymer to contain linkages via both $R_1$ and $R_2$.

As side chains, $R_1$ and $R_2$ may in principle represent any group that is inert in the formation of the supramolecular polymer, for example an alkyl, alkoxy or aryl group, whether or not substituted, or groups containing esters or ethers; the side chain may however also be a polymeric chain. The number of C atoms in these groups is in no way critical and lies for example between 1 and 40 C atoms, in particular between 1 and 20 C atoms. Preferably the side chain is an alkyl group.

As linking units, $R_1$ and $R_2$ may also represent all kinds of shorter or longer chains, for example saturated or unsaturated alkyl chains, siloxane chains, ester chains, ether chains and any chain of atoms used in traditional polymer chemistry, whether or not substituted.

These self-complementary compounds can be easily prepared on a large scale and can be easily modified.

The invention also relates to compounds containing structural elements having the general formula 4.a or 4.b.

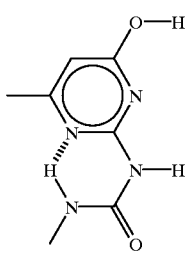

4.a.

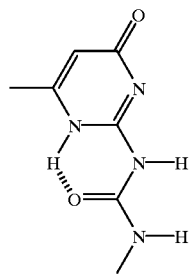

4.b.

where "" stands for an H-bridge.

Polymers according to the invention may be composed in several ways. The polymers may consist substantially of H-bridge-forming monomeric units with a low molecular weight, optionally mixtures of such H-bridge-forming monomeric units, as a result of which an essentially linear polymer may be formed; also conceivable on the other hand are (essentially linear) polymers in which the H-bridge-forming monomeric units are linked to 2 ends of the polymers so that polymeric chains are linked to one another via the H-bridges. In addition, a number of H-bridge-forming monomeric units can be grafted onto polymers, as a result of which a form of cross-linking via H-bridges may be obtained. Mixed forms are of course also possible. Both low- and high-molecular, linear or branched polymers can be used as the polymers, for example polymers known from traditional polymer chemistry, or mixtures of such polymers.

The invention will now be elucidated with reference to the examples; without however being limited thereby.

EXAMPLES

Synthesis Units

The 2-butylureido-4-pyrimidone unit can be quickly prepared by causing precursor isocytosine to react with isocyanate in refluxing pyridine. Isocytosines can in turn be easily prepared from β-keto esters through condensation with guanidine.

β-keto esters can be synthesised in several manners. Two of the most frequently used manners are (a) alkylation of the dianion of (m)ethyl acetoacetate with an alkyl halide, and (b) reaction of an acid chloride with the anion of ethyl acetoacetate, followed by deacylation of an aceto fragment.

The reaction scheme for a is as follows:

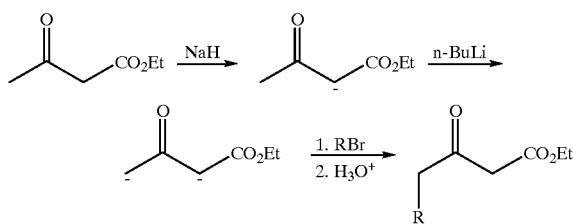

The anion of ethyl acetoacetate is first prepared in THF with the aid of sodium hydride, after which the dianion is prepared with the aid of butyl lithium. This dianion is caused to react with an alkyl halide, in which process it reacts at the 4-position, the most nucleophilic position. Working-up takes place through neutralisation with acid of the monoanion still present.

The reaction scheme for b is as follows:

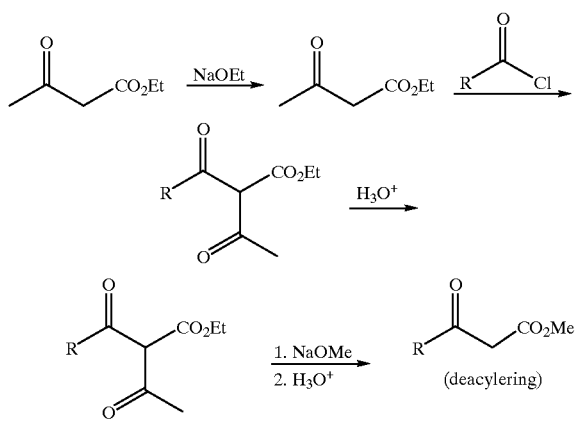

First the anion of the ethyl acetoacetate is prepared in ether using sodium ethoxide in ethanol. This nucleophilic anion attacks the electrophilic carbon of the acid chloride, the chloride being eliminated. At least 2 equivalents of base are required per acid chloride, because the neutral product formed initially immediately donates a proton to the anion of ethyl acetoacetate or ethoxide. An excess of ethyl acetoacetate is also important, because the ethoxide is more nucleophilic than the anion of ethyl acetoacetate. By using an excess of ethyl acetoacetate relative to ethoxide, the undesired formation of an ethyl ester through reaction of the ethoxide with the acid chloride is thus prevented. After the reaction the anion is neutralised with acid. Next, deacylation takes place with the aid of sodium ethoxide in methanol, the ester being largely converted from an ethyl ester into a methyl ester. Sodium ethoxide in methanol is used for the deacylation instead of sodium ethoxide in ethanol, because the deacylation does not proceed well with the latter. It is however not important whether methyl or ethyl ester is formed, in view of the fact that in the formation of the isocytosine (m)ethanol is eliminated anyway.

Experimental Methods

General Experimental Section

Dry tetrahydrofuran (THF) was obtained through distillation in the presence of sodium and benzophenone. Dry toluene was obtained through distillation and freezing. Pyridine, ethanol and dimethylformamide (DMF) (p.a.) were dried using 4 A molecular sieves.

Kiezelgel 60 $F_{254}$ aluminium plates were used for thin-layer chromatography (TLC). UV-active compounds were identified with the aid of 254 nm UV. Merck Kiezelgel 60 with a particle size of 63–200 $\mu$m and Merck Kiezelgel 60H with a particle size of 40–63 $\mu$m were used for column chromatography.

NMR spectra were recorded with the aid of a Varian Gemini (300 MHz) or a Bruker AC400 (400 MHz). Chemical shifts ($\delta$) for both proton and carbon are indicated in ppm relative to tetramethylsilane (TMS).

Multiplicities are indicated by s (singlet), d (doublet), t (triplet), q (quartet), m (multiplet).

Infrared (IR) spectra were recorded with the aid of a Perkin-Elmer 1600 FT-IR spectrometer.

A Perkin-Elmer DSC 7 was used in DSC analysis.

Melting points were determined with the aid of a Jenaval THMS 6000 polarisation microscope.

Example I 2-butylureido-6-methyl-4-pyrimidone

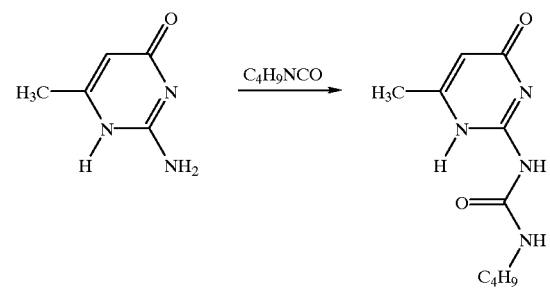

6-methyl-isocytosine (commercially available) was weighed into a flask (1.24 grams, 0.018 mol). The flask was fitted with a reflux condenser with a nitrogen inlet tube and was brought under a nitrogen atmosphere. 50 ml of dry pyridine was added, followed by butyl isocyanate (2 ml, 0.018 mol). The suspension was heated to reflux temperature, during which a clear solution was slowly obtained (after approx. 1 hour). After 2 hours' boiling while refluxing, the solvent was evaporated, after cooling. The white residue was crystallised from 1/1 v/v ethanol/chloroform. Yield 1.63 grams, 66%.

$^1$H-NMR (CDCl$_3$): $\delta$ (ppm): 13.15 (s, 1H), 11.85 (s, 1H), 10.16 (S, 1H), 5.81 (s, 1H), 3.24 (q, 2H), 3.22 (s, 3H), 1.58 (m, 2H), 1.37 (m, 2H), 0.92 (t, 3H). $^{13}$C-NMR (CDCl$_3$): $\delta$ (ppm): 173.0, 156.5, 154.7, 148.1, 106.6, 39.7, 31.5, 20.1, 18.9, 13.7, IR (KBr) (keto form): $\upsilon$ (cm$^{-1}$): 3215, 2954, 2868, 1705, 1666, 1584.

Example II

Ethyl 3-oxo-hexadecanoate

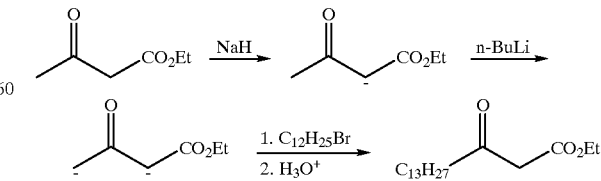

Sodium hydride (60%, 4.42 g, 0.11 mol) was weighed into a dry 3-neck flask (1000 cc). The flask was brought under a nitrogen atmosphere and placed in an ice-salt bath, after which dry THF (250 ml) was added at 0° C. Ethyl acetoacetate (13.02 g, 0.102 mol) was added drop by drop via a dry syringe, at a temperature of between 0 and 5° C. A strongly exothermic reaction took place with gas formation. After 30 minutes' stirring at 0° C., n-butyl lithium (1.6 M, 66 ml, 0.104 mol) was added drop by drop, after which the stirring was continued for 15 min. at 0° C. Dodecyl bromide (127.4 g, 0.110 mol) in dry THF (20 ml) was added via a dry syringe at 0° C. The solution was stirred for 45 min, during which the temperature rose to room temperature and a suspension formed. To this suspension were added concentrated hydrochloric acid (20 ml) in water (600 ml), followed by ether (1000 ml). After extraction, the water layer was once again extracted with ether. The combined ether layers were washed with water 5 times. The ether layer was dried over sodium sulphate, filtered and evaporated. A total of 136.11 grams of crude product was obtained in four such syntheses. NMR showed that the product is a mixture of ethyl 3-oxo-hexadecanoate (61%) and dodecyl bromide (39%), so the corrected ethyl 3-oxo-hexadecanoate yield is 0.29 mol. 72%. The crude product was used as such for the following synthesis.

¹H-NMR (CDCl₃): δ (ppm): 4.16 (t, 2H), 3.38 (s, 2H), 2.52 (t, 2H), 1.82 (m, 2H), 1.58 (m, 2H), 1.25 (m, 21H) 0.85 (t, 3H).

6-Tridecylisocytosine

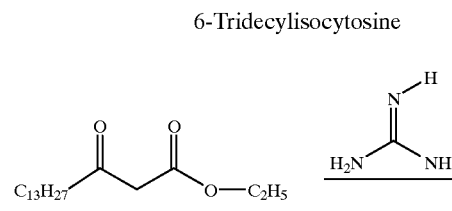

Guanidine carbonate (30.63 g, 0.17 mol) was weighed into a dry 2-neck flask (500 ml). The flask was brought under a nitrogen atmosphere, after which dry ethanol (220 ml) and the crude ethyl 3-oxo-hexadecanoate (136.11 g, 0.29 mol) were added. After refluxing overnight, ethanol (100 ml) was slowly evaporated and the refluxing was continued for another 2 hours. After cooling, hexane (300 ml) was added, followed by water, which caused 6-tridecylisocytosine to precipitate, which could be removed through filtration. This was successively washed with hexane, acetone and water.

The crude product was recrystallised from ethanol with a Norit treatment. The product was obtained as a microcrystalline powder, after thorough drying, 39.68 g (0.142 mol. 48%).

¹H-NMR (DMSO d6): δ (ppm): 10.57 (s, 1H), 7–6 (br, 2H), 5.36 (s, 1H), 2.24 (t, 2H), 1.55 (t, 2H), 1.26 (m, 20H), 0.86 (t, 3H). ¹³C-NMR (DMSO d6): δ (ppm), (388 K): 168.1, 162.7, 155.0, 99.2, 36.1, 30.4, 28.1 (overlapping peaks), 26.6 (overlapping peaks), 21.1, 12.6 IR (KBr): υ (cm⁻¹): 3365, 3146, 2920, 2850, 2713, 1662, 1639, 1553, 1468, 1400. Element analysis: N 14.65% (calc. 14.32%), C 70.91% (calc. 69.58%), H 11.27% (calc. 10.65%). Melting point: 181° C.

2-butylureido-6-tridecyl-4-pyrimidone

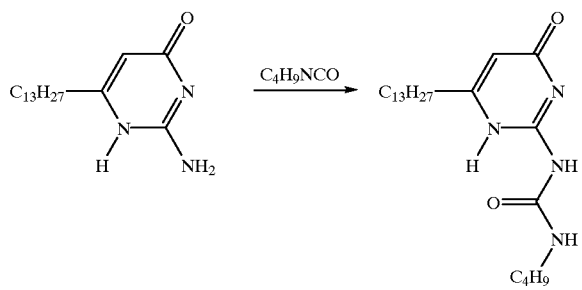

6-tridecylisocytosine (10.22 g, 0.036 mol) was weighed into a dry 2-neck flask (500 ml). The flask was brought under a nitrogen atmosphere, after which dry pyridine (200 ml) and butylisocyanate (6.8 ml, 0.06 mol) were added. After 4 hours' refluxing, the pyridine and the residual butylisocyanate were evaporated.

Recrystallisation from acetone followed by drying resulted in pure 2-butylureido-6-tridecyl-4-pyrimidone as a microcrystalline powder (11.58 g, 0.0295 mol, 82%).

¹H-NMR (CDCl₃): δ (ppm): 13.18 (s, 1H), 11.88 (s, 1H), 10.17 (s, 1H), 5.82 (s, 1H), 3.24 (q, 2H), 2.45 (t, 2H), 1.62 (m, 4H), 1.31 (m, 22H), 0.90 (m, 6H). ¹³C-NMR (CDCl₃): δ (ppm): 174, 157, 155, 152, 106, 41, 33, 32, 30 (overlapping peaks), 24, 21, 15, 14. IR (Kbr) (enol form): υ (cm⁻¹): 3200, 3132, 2920, 2849, 2480, 1666, 1610, 1557, 1453. Element analysis: N 14.35% (calc. 14.27%), C 66.54% (67.31%), H 10.41% (10.27%). Melting point 118° C.

Example III 2-phenylureido-6-tridecyl-4-pyrimidone

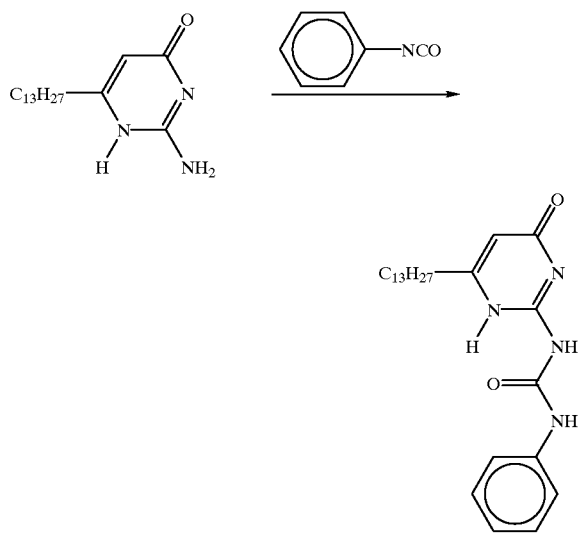

6-tridecylisocytosine (0.28 g, 0.001 mol) was weighed into a dry 2-neck flask (25 ml). The flask was brought under a nitrogen atmosphere, after which dry pyridine (5 ml) and phenylisocyanate (0.21 ml, 0.0018 mol) were added. After 4 hours' refluxing the mixture was cooled to room temperature and diluted with acetone. The precipitated white powder was filtered.

Recrystallisation from acetic acid resulted in pure 2-phenylureido-6-tridecyl-4-pyrimidone as a microcrystalline powder (0.14 g, 0.00034 mol, 34%).

$^1$H-NMR (CDCl$_3$): δ (ppm): 12.99 (s, 1H), 12.21 (s, 1H), 12.19 (s, 1H), 7.70 (d, 2H), 7.34 (t, 2H), 7.09 (t, 1H), 5.83 (s, 1H), 2.31 (t, 2H), 1.53 (m, 2H), 1.26 (m, 20H), 0.90 (t, 3H). $^{13}$C-NMR (CDCl$_3$): δ (ppm): 173.0, 154.6, 152.8, 138.2, 128.9, 123.9, 120.6, 106.0, 32.5, 31.9, 29.6, 29.6, 29.4, 29.4 (overlapping peaks), 29.2, 28.8, 26.6, 22.7, 14.1. IR (KBr) (keto form): υ (cm$^{-1}$): 3133, 3022, 2918, 2849, 1701, 1654, 1560, 1500.

Example IV 2-(p-nitrophenyl)ureido-6-tridecyl-4-pyrimidone

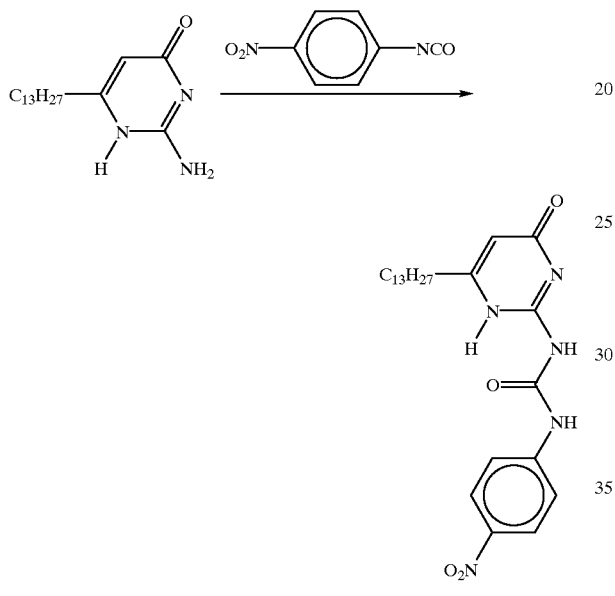

6-tridecylisocytosine (0.44 g, 0.00015 mol) was weighed into a dry 2-neck flask (100 ml). The flask was brought under a nitrogen atmosphere, after which dry pyridine (20 ml) and p-nitrophenylisocyanate (0.27 grams, 0.00016 mol) were added. After refluxing overnight, during which initially an almost clear solution was obtained, but later a suspension, the mixture was evaporated. The product is very poorly soluble. Recrystallisation from acetic acid followed by drying resulted in pure 2-(p-nitrophenyl)ureido-6-tridecyl-4-pyrimidone as a microcrystalline powder $^1$H-NMR (CDCl$_3$, reflux): δ (ppm): 12.8 (s, 1H), 12.7 (s, 1H), 12.4 (s, 1H) 8.20 (d, 2H), 7.93 (d, 2H), 6.0 (s, 1H), 2.56 (t, 2H), 1.71 (m, 2H), 1.27 (m, 20H), 0.87 (t, 3H).

Example V 6-phenylisocytosine

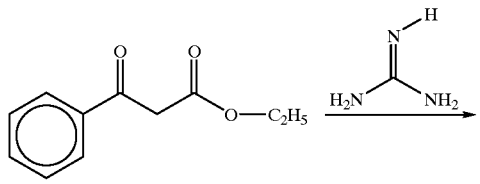

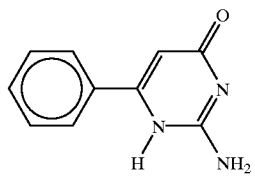

Guanidine carbonate (9.09 g, 0.05 mol) was weighed into a 2-neck flask (250 ml), after which the flask was brought under a nitrogen atmosphere. Next, dry ethanol (100 mol) was added, followed by ethyl benzoylacetate (commercial, 19.2 g, 0.10 mol). The mixture was refluxed overnight. After cooling to room temperature, 6-phenylisocytosine was removed through filtration, washed with ethanol, then water, then again ethanol and dried (12.02 g, 0.064 mol, 64%).

$^1$H-NMR (DMSO d6): δ (ppm): 10.84 (br, 1H), 7.94 (m, 2H), 7.43 (m, 3H), 6.62 (br, 2H), 6.11 (s, 1H). $^{13}$C-NMR (DMSO d6): (388K) δ (ppm): 162.8, 162.2, 155.2, 137.1, 128.9, 127.4, 125.9, 97.4. IR (KBr): υ (cm$^{-1}$): 3350, 3087, 2956, 1658, 1502, 1476, 1380. Element analysis: N 23.03% (calc. 22.45%), C 64.29% (calc. 64.16%), H 5.06% (calc. 4,85%). Melting point: 312° C.

Example VI 2-butylureido-6-phenyl-4-pyrimidone

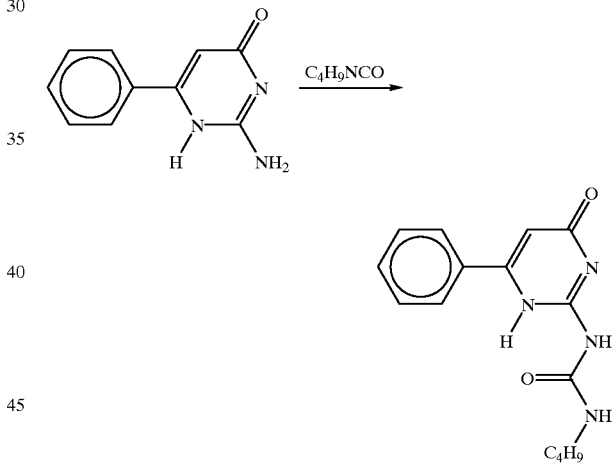

6-phenylisocytosine (1.93 g, 0.010 mol) was weighed into a dry 2-neck flask (100 ml), after which the flask was brought under a nitrogen atmosphere. Next, pyridine (40 ml) was added, and butylisocyanate (1.69 ml, 0.015 mol). After 4 hours' refluxing, during which the suspension gradually changed into a clear solution, the pyridine and the butylisocyanate were evaporated. The white powder was suspended in acetone and removed through filtration. To purify 2-butylureido-6-phenyl-4-pyrimidone, it was recrystallised from a 1:1 (v:v) ethanol/chloroform mixture. The yield obtained after filtration and drying was 2.34 g (0.0082 mol, 82%).

$^1$H-NMR (CDCl$_3$): δ (ppm) (keto peaks): 13.9 (s, 1H), 12.1 (s, 1H), 10.2 (s, 1H), 7.7 (m, 2H), 7.5 (m, 3H), 6.4 (s, 1H), 3.3 (m, 2H), 1.7 (q, 2H), 1.5 (q, 2H), 0.9 (t, 3H). $^{13}$C-NMR (54° C.) (CDCl$_3$): (enol and keto peaks) δ (ppm): 173.2, 157.0, 155.4, 148.8, 137.0, 131.1, 130.7, 129.6, 128.9, 126.9, 125.8, 104.4, 39.9, 31.6, 29.7, 20.2, 13.7.

IR(KBr): (enol form): 3217, 31,37, 3029, 2958, 2873, 2587, 2511, 1658, 1614, 1557, 1444, 1327.

Both needles and plates could be obtained in crystallisation from chloroform by means of evaporation. The IR of the plates is identical to that of the product obtained from ethanol-chloroform (enol form). In the keto form the needles are: υ (cm$^{-1}$) 3202, 3012, 2959, 2871, 1692, 1656, 1588, 1528, 1453, 1255. Element analysis: N 20.52% (calc. 19.57%), C 62.50% (calc. 62.92%), H 5.30% (calc. 6.34%). Melting point: enol powder: 245° C. Enol plate crystals 114° C. phase transition, 245° C. melting+sublimation, subsequently solidifying. Keto crystals: 85–120° C. crystals splinter, 245° C. melting+sublimation, subsequently solidifying.

Example VII 2-(1,6-Hexadiyl)-6-tridecyl-4-pyrimidone

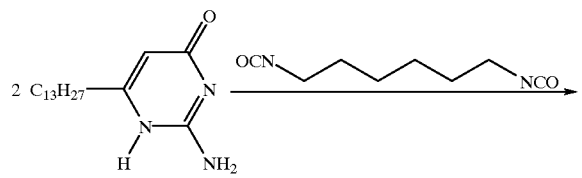

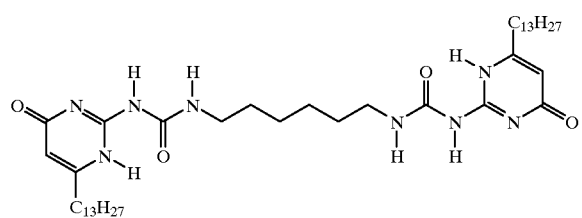

6-tridecylisocytosine (11.20 g, 0.04 mol) was weighed into a 2-neck flask (250 ml), after which the flask was brought under a nitrogen atmosphere. Pyridine (80 ml) and toluene (10 ml) were added to the flask. The mixture was heated to reflux temperature and a clear solution was obtained. Approx. 10 mol solvent was azeotropically removed through distillation. After cooling to room temperature hexane diisocyanate (3.33 g, 0.0198 mol) was added. The mixture was refluxed for 3 days, after which the addition of acetone resulted in the formation of a suspension, from which the product could be removed through filtration (93% yield). 2-(1,6-hexadiyl)-6-tridecyl-4-pyrimidone was purified by means of column chromatography with the aid of a flash silica column using as an eluant first 3% ethanol in chloroform, which was later gradually increased to 5% ethanol in chloroform. The substance showed tailing in the column, so only the initial fractions were pure. The fractions containing pure product were for the greater part evaporated and precipitated in acetone. Impure column fractions were once again separated in the same manner. Thorough drying resulted in a total overall yield of 66%. For optimum polymer properties it proved to be extremely important to have the substance in a very high purity.

$^{1}$H-NMR (CDCl$_3$): δ (ppm): 13.18 (s, 2H), 11.88 (s, 2H), 10.18 (s, 2H), 5.82 (s, 2H), 3.23 (s, 4H), 2.45 (t, 4H), 1.63 (d, 8H), 1.25 (m, 44H), 0.88 (t, 6H). $^{13}$C-NMR (CDCl$_3$): δ (ppm): 173.2, 156.6, 154.7, 152.4, 105.8, 40.0, 32.7, 31.9, 29.4, 29.3, 29.1 (overlapping peaks), 26.8, 22.7, 14.1. IR (KBr): υ (cm$^{-1}$): 3220, 3036, 2924, 2852, 2605, 1700, 1661, 1586, 1524, 1460, 1252. Element analysis: N 14.62% (calc. 14.84%), C 67.25% (calc. 66.81%), H 9.77% (calc. 9.88%). Melting point: from approx. 100° C. 2-(1,6-hexadiyl)-6-tridecyl-4-pyrimidone became liquid but it did remain birefringent, after which it became isotropic at approx. 180° C. When cooled (slowly or quickly) the substance remained in a vitreous phase which did not crystallise (not even after a few weeks).

Example VIII 2-(1,6-trimethylhexadiyl)-6-tridecyl-4-pyrimidone

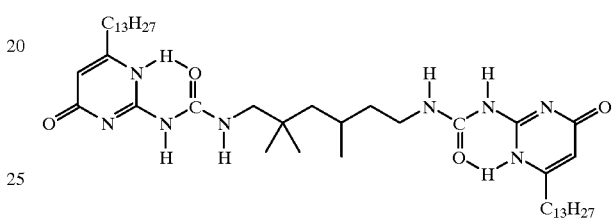

1.76 g (8.37 mmol) of trimethyl-1,6-diisocyanatohexane (a mixture of 2,4,4- and 2,2,4-) in 5 ml of dry pyridine was added to 4.82 g (16.4 mmol) of tridecylisocytosine, under an argon atmosphere. The reaction mixture was stirred for one night at 120° C. After it had cooled, the reaction mixture was precipitated in 250 ml of acetone. Next, the precipitate was purified via column chromatography (silica gel, 1% MeOH in chloroform) followed by recrystallisation from 300 ml of ethyl acetate. This resulted in the formation of 4.39 g (67%) of product, a highly viscous pale yellow oil.

$^{1}$H-NMR (CDCl$_3$): d (ppm): 12.99 (br s, 2H), 11.66 (br s, 2H), 9.90 (br s, 2H), 5.55 (s, 2H), 2.99 (s, 4H), 2.22 (t, 4H), 1.41 (d, 8H), 1.06 (m, 53H), 0.67 (t, 6H). $^{13}$C-NMR (CDCl$_3$): d (ppm): 172.8, 156.4, 154.6, 152.1, 105.6, 35.7, 32.8, 32.5, 31.8, 29.4, 29.3, 29.0 (overlapping peaks), 27.1, 26.8, 25.0, 22.5, 22.2, 20.7, 14.0.

Example IX 2-amino-6-(3-butenyl)-4-pyrimidone

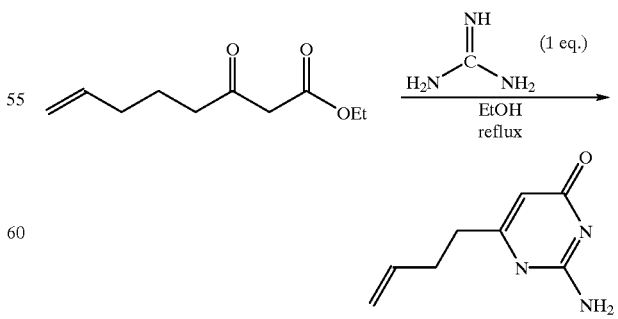

Guanidine carbonate (14.05 g; 0.078 mol; E. Merck AG) was weighed into a dry two-neck flask. Nitrogen gas was passed through the flask, after which dry ethanol (160 ml) was added. The crude ethyl 3-oxo-6-heptenoate obtained in the previous step was added during the stirring. After refluxing for one night, the ethanol was partially evaporated and water (50 ml) was added. The white precipitate thus obtained was removed through filtration, washed with water, cold ethanol and cold acetone, and dried in a vacuum (η=38%).

1H NMR (DMSO $d_6$): δ10.74 (s, 1H, NH), 6.54 (s, 2H, NH), 5.80 (m, 1H, $\underline{H}C=CH_2$), 5.40 (s, 1H, alkylidene), 5.01 (m, 2H, $\underline{H}_2C=C$), 2.3 (m, 2*2H, $2CH_2$) ppm. $^{13}C$ NMR (DMSO $d_6$): δ167, 164.51, 155.84, 137.73, 115.23, 100.04, 35.63, 31.52 ppm.

Element analysis: $C_8H_{11}N_3O$; C 57.29% (calc. 58.17%), H 6.71% (6.71%), N 25.85% (25.44%).

Example X 6-(3-butenyl)-2-butylureido-4-pyrimidone

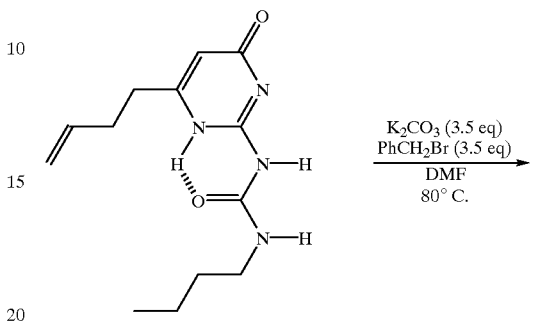

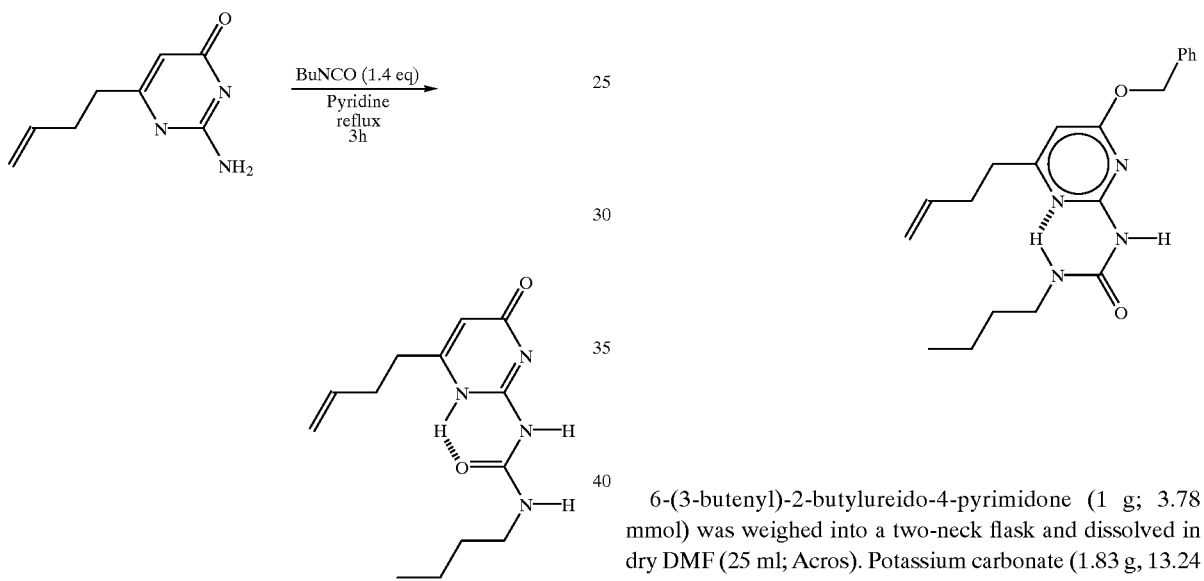

2-amino-6-(3-butenyl)4-pyrimidone (3 g; 18.16 mmol) was weighed into a dry two-neck flask and dissolved in dry pyridine (36 ml) with heating, in a nitrogen atmosphere. After everything had dissolved, n-butyl isocyanate (2.86 ml; 25.43 mmol; Aldrich) was added via a syringe. After three hours' stirring with reflux, the pyridine was evaporated. The product was isolated with the aid of crystallisation from ethanol (η=87%).

$^1$H-NMR (CDCl$_3$): δ13.24 (s, 1H, NH), 11.87 (s, 1H, NH) 10.14 (s, 1H, NH), 5.84 (s, 1H, alkylidene), 5.79 (m, 1H, —$\underline{H}C=CH_2$), 5.09 (m, 2H, $C\underline{H}_2=CH—$), 3.25 (m, 2H, $CH_2$, butyl), 2.58 (t, 2H, $CH_2$), 2.43 (m, 2H, $CH_2$) 1.59 (m, 2H, $CH_2$, butyl), 1.39 (m, 2H, $CH_2$, butyl), 0.96 (t, 3H, $CH_3$) ppm.

$^{13}C$ NMR (CDCl$_3$): δ173.05, 156.56, 154.71, 151.38, 135.13, 116.94, 106.08, 39.78, 31.94, 31.53, 30.78, 20.15, 13.75 ppm.

Element analysis: $C_{13}H_{20}N_4O_2$; C 58.78% (calc. 59.07%), H 7.67% (7.63%), N 21.56% (21.20%).

Example XI 4-benzyloxy-6-(3-butenyl)-2-butylureidopyrimidine

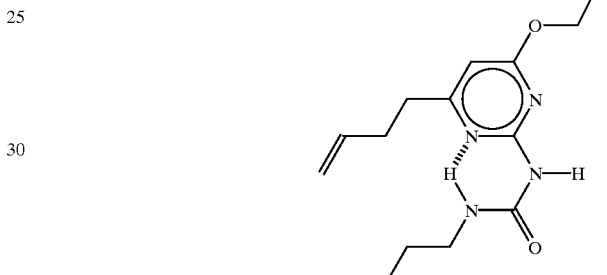

6-(3-butenyl)-2-butylureido-4-pyrimidone (1 g; 3.78 mmol) was weighed into a two-neck flask and dissolved in dry DMF (25 ml; Acros). Potassium carbonate (1.83 g, 13.24 mmol) was subsequently weighed and added. Benzyl bromide (1.58 ml; 13.24 mmol; Acros) was slowly added drop by drop via a syringe, with vigorous stirring. The whole was stirred at 80° C. for one night. After that, a generous amount of acetone was added to the reaction mixture, after which potassium carbonate was removed through filtration and rinsed with acetone. Water was added to the filtrate until a precipitate formed. The product was subsequently crystallised from ethanol/water (3/1) and recrystallised from hexane (η=78%).

$^1$H NMR (CDCl$_3$): δ9.21 (s, 1H, NH), 7.39 (m, 5H, Ph) 7.13 (s, 1H, NH), 6.22 (s, 1H, alkylidene), 5.84 (m, 1H, —$\underline{H}C=CH_2$), 5.33 (s, 2H, $C\underline{H}_2$—Ph), 5.10 (m, 2H, $C\underline{H}_2=CH—$), 3.37 (m, 2H, $CH_2$, butyl), 2.70 (t, 2H, $CH_2$), 2.46 (m, 2H, $CH_2$), 1.59 (m, 2H, $CH_2$, butyl), 1.45 (m, 2H, $CH_2$, butyl), 0.96 (t, 3H, $CH_3$) ppm.

Example XII di[4-benzyloxy-6-butyl-2-butylureidopyrimidine]-hexamethyltrisiloxane

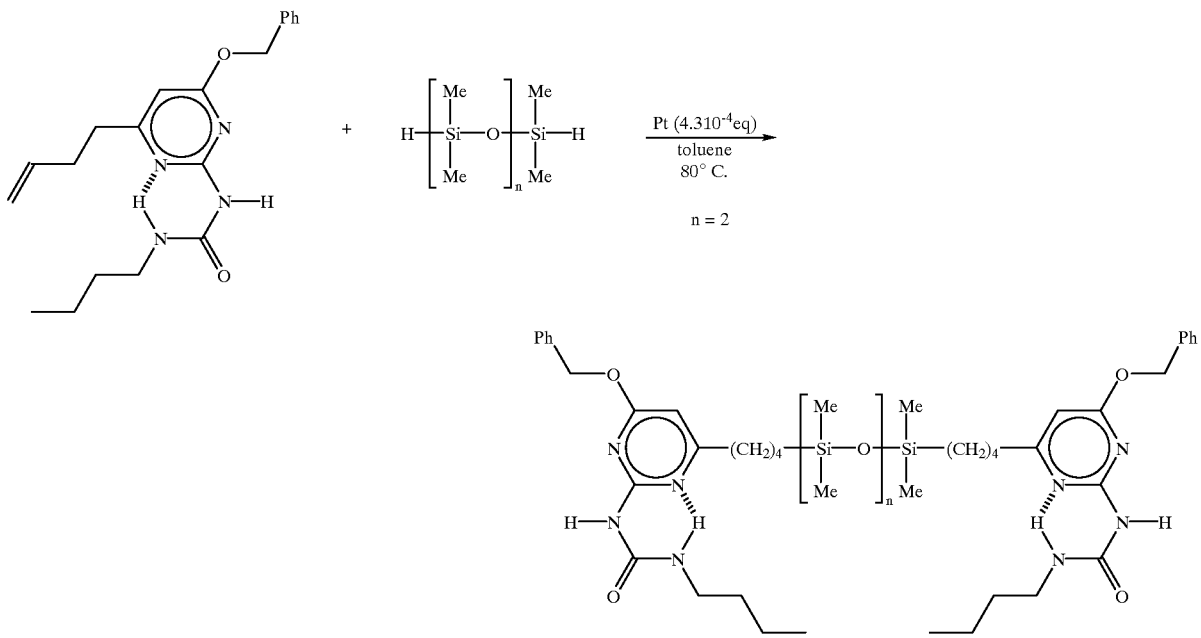

4-benzyloxy-6-(3-butenyl)-2-butylureidopyrimidine (0.177 g; 0.5 mmol) was weighed into a dry 10-ml Schlenk vessel, after which the whole was introduced into the glove box via an air lock. Hexamethyltrisiloxane (0.052 g; 0.25 mmol) was weighed into this. A solution of the platinum catalyst (2.1%–2.4% in xylene, 1 μl, 0.12 μmol) in dry toluene was prepared and added to the pyrimidine/siloxane mixture. Dry toluene was finally added until the total amount of toluene was approx. 1 ml. After one night's stirring at 80° C., toluene was removed through evaporation using a Rotavapor. The product was ultimately isolated with the aid of column chromatography (eluant: 7% THF in $CHCl_3$).

$^1$H NMR ($CDCl_3$): δ9.30 (s, 2H, NH), 7.34 (m, 10H, Ph) 7.34 (s, 2H, NH), 6.19 (s, 2H, alkylidene), 5.31 (s, 4H, C$H_2$—Ph), 3.36 (m, 4H, $CH_2$, butyl), 2.57 (m, 4H, $CH_2$), 1.68 (6m, 4H, $CH_2$), 1.57 (m, 4H, $CH_2$, butyl), 1.41 (m, 4H, $CH_2$ butyl), 1.41 (m, 4H, $CH_2$), 0.96 (t, 6H, $CH_3$), 0.56 (t, 4H, $CH_2$), 0.06 (s, 12H, Si-$CH_3$), −0.01 (s, 6H, Si-$CH_3$) ppm.

Example XIII di[6-butyl-2-butylureido-4-pyrimidone] polydimethylsiloxane

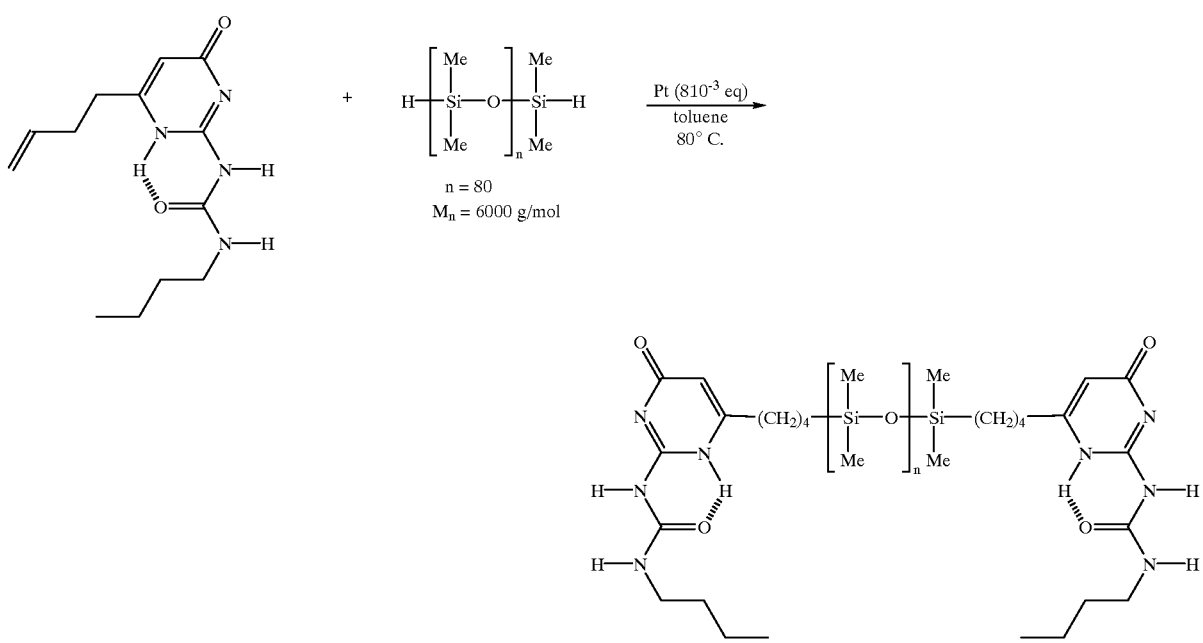

6-(3-butenyl)-2-butylureido-4-pyrimidone (0.0535 g; 0.2 mmol) was weighed into a dry 10-ml Schlenk vessel, after which the whole was introduced into the glove box via an air lock. Polydimethyltrisiloxane (PDMS) (0.168 g; 0.028 mmol; ABCR) was weighed into this. A solution of the platinum catalyst (platinum divinyl tetramethyldisiloxane complex, 2.1%–2.4% in xylene; 2 μl; 0.24 μmol; ABCR) in dry toluene was prepared and added to the pyrimidine/PDMS mixture. Finally, dry toluene was added until the total amount of toluene was approx. 1 ml. After one night's stirring at 80° C. toluene was removed through evaporation with the aid of the Rotavapor. The product was ultimately isolated with the aid of column chromatography (eluant: 7% THF in CHCl$_3$).

$^1$H NMR (CDCl$_3$): δ13.21 (s, 2H, NH), 11.89 (s, 2H, NH) 10.17 (s, 2H, NH), 5.84 (s, 2H, alkylidene), 3.25 (q, 4H, CH$_2$ butyl), 2.47 (t, 4H, CH$_2$), 1.68 (m, 4H, CH$_2$), 1.59 (m, 4H, CH$_2$, butyl), 1.41 (m, 4H, CH$_2$, butyl), 1.41 (m, 4H, CH$_2$), 0.94 (t, 6H, CH$_3$), 0.56 (t, 4H, CH$_2$), 0.06 (s, n*6H, Si—CH,) ppm.

suspension was vigorously stirred. At a temperature of 0° C., ethyl acetoacetate (6.96 g; 55 mmol; Merck-Schuchardt) was added drop by drop via a dry syringe. After 15 minutes' stirring at 0° C. n-butyl lithium (1.6 M in hexane, 36.1 ml; 57.75 mol; Acros) was added, again drop by drop via a syringe, at 0° C. The whole was stirred for 15 minutes. In the meantime a solution was prepared of α,α'-dibromo-p-xylene (6.6 g; 25 mmol; Aldrich) in dry THF (66 ml), after which this solution was added to the dianion mixture via a dropping funnel, drop by drop, at 0° C. After 10 minutes' reaction the whole was quenched with the aid of a mixture of concentrated HCl (10 ml), water (25 ml) and ether (75 ml; technical grade). The water phase was separated from the organic phase. Next, the water layer was washed once with 100 ml of ether. The combined organic layers were then washed 4 times using 100 ml of water and once using a saturated NaCl solution. The ether layer was subsequently dried with the aid of sodium sulphate and filtered and the ether was evaporated via the Rotavapor (10.84 g). The crude product was however used as such in the synthesis of p-di-(2-amino-6-(ethyl)-4-pyrimidone) benzene.

$^1$H NMR (CDCl$_3$): δ7.07 (s, 4H, Ar—H), 4.20 (q, 4H, OCH$_2$), 3.47 (s, 4H, CH$_2$), 2.87 (m, 4H, CH$_2$), 2.87 (m, 4H, CH$_2$), 1.28 (t, 6H, CH$_3$) ppm.

$^{13}$C NMR (CDCl$_3$): δ201, 166.96, 138.30, 128.67, 61.24, 49.27, 44.33, 28.83, 13.96 ppm.

p-di-(2-amino-6-(ethyl)-4-pyrimidone) benzene

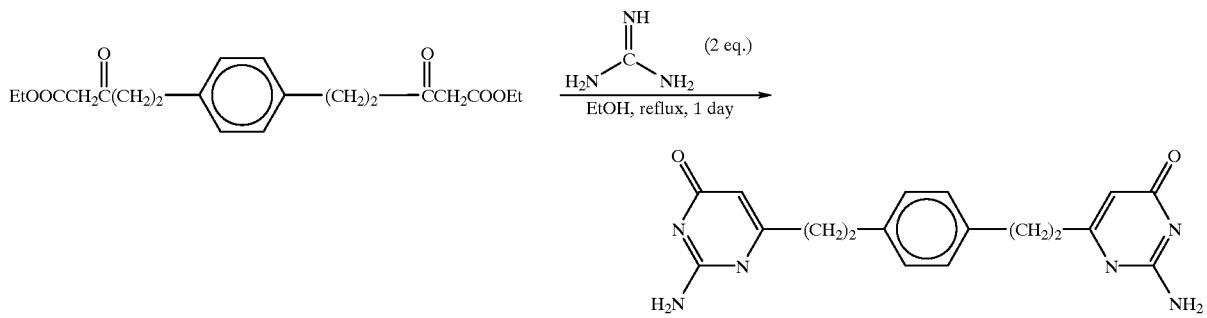

Example XIV p-Di-(ethyl 3-oxo-5-pentanoate) benzene

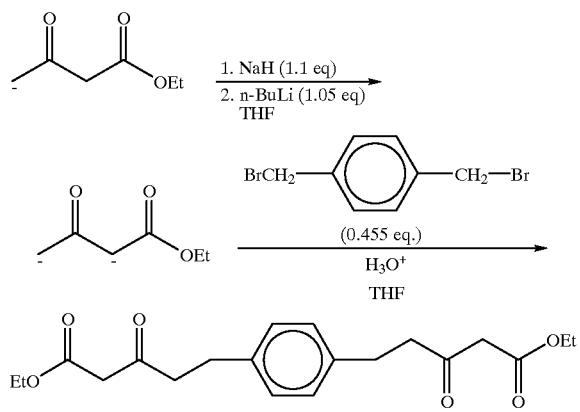

NaH (60 wt.%, 2.42 g; 60.5 mmol) was weighed into a three-neck flask fitted with a septum and a thermometer. Nitrogen gas was passed through and the whole was placed in an ice/salt bath. Dry THF (125 ml) was added and the Guanidine carbonate (4.54 g; 25 mmol; E. Merck AG) was weighed into a dry two-neck flask. Nitrogen gas was passed through the flask, after which dry ethanol (50 ml) was added. The crude p-di-(ethyl 3-oxo-6-heptenoate) benzene obtained in the previous step was added during the stirring. After one night's refluxing, the solid substance was removed through filtration and washed with water, ethanol and acetone. The product was subsequently purified via crystallisation from acetic acid ($\eta_{overall}$=38%).

$^1$H NMR (DMSO d$_6$): δ10.67 (s, 2H, NH), 7.11 (s, 4H, Ar—H), 6.51 (s, 4H, NH$_2$), 5.40 (s, 2H, alkylidene), 2.81 (t, 4H, Ar—CH$_2$) 2.50 (t, 4H, CH$_2$) ppm.

Example XV 6-(3-butenyl)-2-butylureido-4-pyrimidone

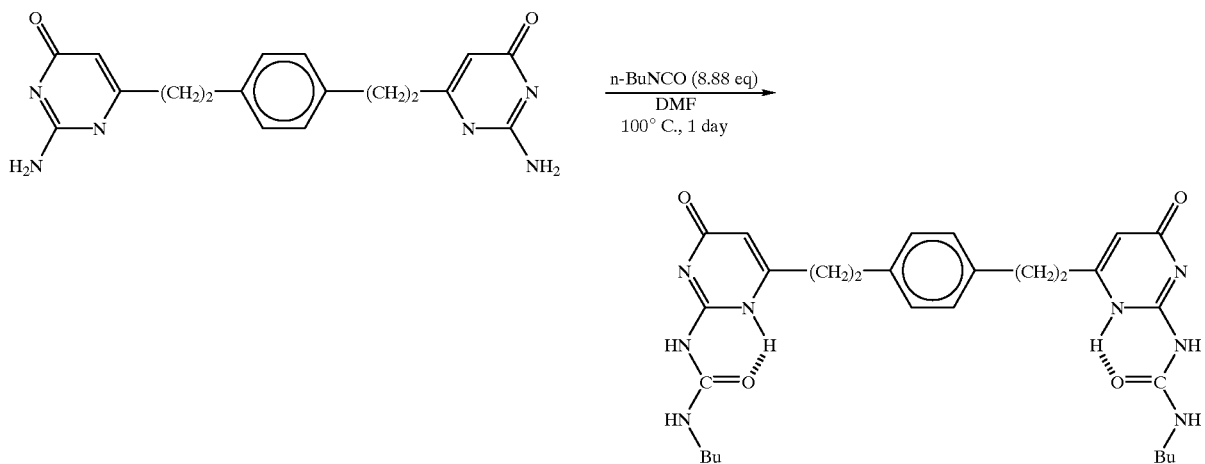

p-di-(2-amino-6-ethyl-4-pyrimidone) benzene (1.76 g; 5 mmol) was weighed into a dry two-neck flask and mixed with dry DMF (25 ml), with heating, in a nitrogen atmosphere. n-butylisocyanate (5 ml; 44.4 mmol; Aldrich) was added to this suspension via a syringe. After 24 hours' stirring at 100° C. a dash of acetone was added. The white precipitate was removed through filtration, washed with DMF and then with acetone, and was finally dried in a vacuum ($\eta$=60%).

$^1$H NMR (DMSO d$_6$): δ11.53 (s, 2H, NH), 9.67 (s, 2H, NH) 7.41 (s, 2H, NH), 7.12 (s, 4H, Ar—H) 5.76 (s, 2H, alkylidene), 3.14 (m, 4H, CH$_2$, butyl), 2.84 (m, 4H, CH$_2$), 2.64 (t, 4H, CH$_2$), 1.46 (m, 4H, CH$_2$, butyl), 1.30 (m, 4H, CH$_2$, butyl), 0.89 (t, 6H, CF$_3$) ppm.

Example XVI

Determination of the Viscosities of Solutions of A in Chloroform in the Presence of B Solutions of A in chloroform have a substantially increased viscosity. If this viscosity is caused by linear linking of A by means of hydrogen bridges, the viscosity will decrease when compound B is added, because this compound can complex on one side only, and prevents further growth of the chain by complexing with A.

A stock solution containing about 40 mM of A was prepared by dissolving 757 milligrams of A in 25 milliliters of chloroform. The viscosity of this solution was determined by determining the time of outflow in an Ubbelohde viscometer in a water bath that was kept at a constant temperature of 20° C. From the stock solution a second chloroform solution was prepared, which contained the same amount of A plus a precisely known amount of compound B. Amounts of this second solution were subsequently added to the viscometer portion by portion, so that solutions with a constant concentration of A and an increasing series of concentrations of the chain terminator B were obtained (see the table). After each addition, the solution obtained was mixed until it was homogeneous and the viscosity was calculated by measuring the time of outflow and using the necessary time correction factor. Finally, the viscosity of the chloroform used was measured so as to be able to determine relative viscosities. The results of this experiment are presented in the following table:

Table: viscosity of a solution of A in chloroform at 25° C. as a function of the added amount of B

| Conc. B conc. A | time of outflow (s) | viscosity $\eta$ (Pa s) | relative viscosity |
|---|---|---|---|
| 0 | 274.7 | 4.04 | 7.48 |
| 0.00094 | 254.7 | 3.74 | 6.93 |
| 0.00187 | 237.2 | 3.48 | 6.44 |
| 0.00373 | 212.5 | 3.12 | 5.78 |
| 0.00736 | 179.1 | 2.63 | 4.87 |
| 0.0096 | 158.3 | 2.29 | 4.24 |
| 0.0143 | 144.9 | 2.12 | 3.93 |
| 0.0191 | 129.0 | 1.93 | 3.57 |
| 0.0385 | 103.0 | 1.53 | 2.83 |
| 0.0746 | 84.8 | 1.238 | 2.29 |
| 0.145 | 73.5 | 1.04 | 1.93 |
| chloroform | 45.6 | 0.54 | 1 |

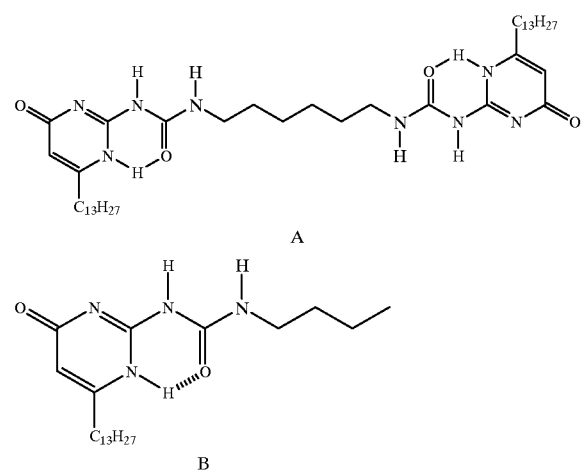

The experiment shows that a substantial reduction in viscosity is observed even when only very small amounts of B are added. The strength of the effect indicates that molecules A in chloroform a) form linear polymer chains and b) that these chains have an average length of several hundreds of molecules.

Material Properties of A

Compound A, obtained through precipitation of a chloroform solution in acetone, is a white powder that melts at 200° C. The viscosity of the melt is comparable with that of glycerol at room temperature. During cooling the viscosity gradually increases, until a leathery, flexible substance forms. Long, highly flexible threads can easily be drawn from the supercooled melt above 100°. Both the threads and the bulk solid become noticeably brittle after a few minutes at room temperature. After a few hours at room temperature the material has become brittle. These properties are typically those of a thermoplastic polymer and are entirely uncommon in compounds with a low molecular weight.

What is claimed:

1. A polymer comprising monomeric units linked via 4 H-bridges and bound within said polymer via a different bond.

2. A polymer according to claim 1, wherein the monomeric units are self-complementary.

3. A polymer according to claim 1, wherein the monomeric units constitute an essentially flat structure.

4. A polymer according to claim 1, wherein monomeric units constitute an essentially flat structure.

5. A polymer according to any one of claims 4 or 1–3, wherein monomeric units contain a structural element having the general form (1) or (2)

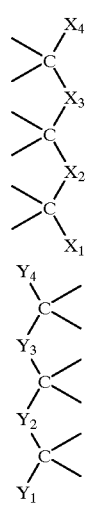

(1)

(2)

in which the C—$X_i$ (i=1 to 4) and the C—$Y_i$ (i=1 to 4) linkages each represent a single or double bond and $X_i$ represent donors or acceptors that form H-bridges with the H-bridge-forming monomeric unit containing a corresponding structural element (2) linked to them, with $Y_i$ representing an acceptor if $X_i$ represents a donor, and vice versa.

6. Polymer according to claim 5, wherein donors and acceptors are O, S or N atoms.

7. A monomeric unit containing a structural element having the general formula

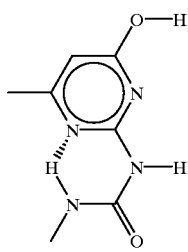

(4.a)

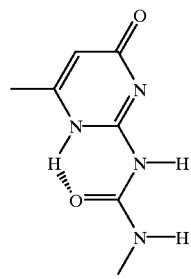

(4.b)

where ⁞⁞⁞⁞⁞ represents an H-bridge.

8. A polymer according to claim 6, wherein $X_1$ and $X_4$ are donors and $X_2$ and $X_3$ are acceptors.

9. A polymer according to claim 5, comprising a monomeric unit having the general structure (3.a) or (3.b)

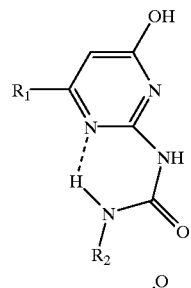

(3.a)

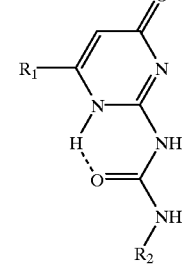

(3.b)

where - - - - - represents an H-bridge, $R_1$ a structural element linking the monomeric unit with another monomeric unit (linking unit) and $R_2$ a side chain, or $R_2$ represents a linking unit and $R_1$ a side chain, or $R_1$ and $R_2$ both represent a linking unit.

10. A polymer according to claim 6, comprising a monomeric unit having the general structure (3.a) or (3.b)

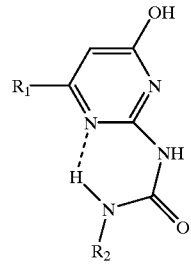

(3.a)

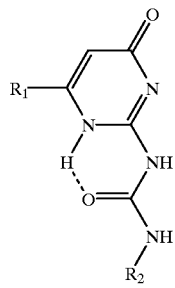

where - - - - - represents an H-bridge, $R_1$ a structural element linking the monomeric unit with another monomeric unit (linking unit) and $R_2$ a side chain, or $R_2$ represents a linking unit and $R_1$ a side chain, or $R_1$ and $R_2$ both represent a linking unit.

11. A polymer according to claim 8, comprising a monomeric unit having the general structure (3.a) or (3.b)

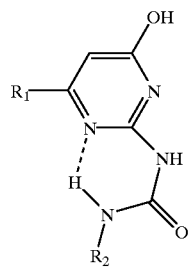

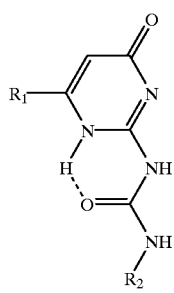

where - - - - - represents an H-bridge, $R_1$ a structural element linking the monomeric unit with another monomeric unit (linking unit) and $R_2$ a side chain, or $R_2$ represents a linking unit and $R_1$ a side chain, or $R_1$ and $R_2$ both represent a linking unit.

12. A polymer according to claim 1, wherein said polymer is a linear polymer.

13. A polymer according to claim 12, wherein said monomeric units only have a covalent bond on one side, and a 4 H-bridge bound on the other side.

14. A polymer according to claim 1, wherein said different bond is a covalent bond.

* * * * *